(12) United States Patent
Shinoki et al.

(10) Patent No.: US 6,726,881 B2
(45) Date of Patent: Apr. 27, 2004

(54) MEASUREMENT CHIP FOR SURFACE PLASMON RESONANCE BIOSENSOR

(75) Inventors: Hiroshi Shinoki, Asaka (JP); Osamu Seshimoto, Asaka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/230,340

(22) Filed: Aug. 29, 2002

(65) Prior Publication Data

US 2003/0073245 A1 Apr. 17, 2003

(30) Foreign Application Priority Data

Sep. 3, 2001 (JP) ......................... 2001-265483

(51) Int. Cl.[7] ........................ G01N 21/75; G01N 33/00
(52) U.S. Cl. ................. 422/82.11; 422/82.05; 422/82.06; 436/72
(58) Field of Search ............... 422/82.05–82.11; 436/72, 164–172

(56) References Cited

U.S. PATENT DOCUMENTS

| | | | |
|---|---|---|---|
| 5,242,828 A | 9/1993 | Bergstrom et al. | |
| 5,436,161 A | 7/1995 | Bergstrom et al. | |

FOREIGN PATENT DOCUMENTS

| | | | | |
|---|---|---|---|---|
| JP | 3-164195 A | | 7/1991 | |
| JP | 4-501605 A | | 3/1992 | |
| JP | 5-288672 A | | 11/1993 | |
| JP | 8-193948 A | | 7/1996 | |
| JP | 2815120 B2 | | 8/1998 | |
| JP | 10267930 A | * | 10/1998 | ......... G01N/33/543 |
| WO | WO 88/06725 A1 | | 9/1988 | |
| WO | WO 88/06726 A1 | | 9/1988 | |
| WO | WO 90/05303 A1 | | 5/1990 | |

OTHER PUBLICATIONS

Katsunori Kojima et al.; Shika–Zairyo (Dental Materials & Appliances), vol. 6(5), pp. 702–707 (1987). (English Abstract).
Yoshinori Kadoma et al.; Shika–Zairyo (Dental Materials & Applicances), vol. 11(3), pp. 430–435 (1992). (English Abstract).
Yoshinori Kadoma, Shika–Zairyo (Dental Materials & Appliances), vol. 11(6), pp. 891–898 (1992). (English Abstract).
Ralph G. Nuzzo et al.; J. Am. Chem., Soc., 1983, vol. 105, pp. 4481–4483.
Victor H. Perez–Luna et al.; J. Am. Chem., Soc., 1999, vol. 121, pp. 6469–6478.
Yoshinori Kadoma, Shika–Zairyo (Dental Materials & Applicances), vol. 12(5), pp. 630–636 (1993). (English Abstract).

* cited by examiner

Primary Examiner—Yelena G. Gakh
(74) Attorney, Agent, or Firm—Birch, Stewart, Kolasch & Birch, LLP

(57) ABSTRACT

The present invention provides a measurement chip for a surface plasmon resonance biosensor, which comprises a transparent substrate, a metal membrane located on the transparent substrate and an organic silicon membrane immobilized on the metal membrane and in which the organic silicon membrane is immobilized on the metal membrane via a functional group capable of binding with atoms on the surface of a metal. The measurement chip for a biosensor of the present invention can easily be produced. Using the measurement chip of the present invention, a target substance can be measured with good sensitivity, even if only a small amount of physiologically active substance is immobilized.

8 Claims, No Drawings

MEASUREMENT CHIP FOR SURFACE PLASMON RESONANCE BIOSENSOR

TECHNICAL FIELD

The present invention relates to a measurement chip for a surface plasmon resonance biosensor, a method for producing the chip, and the use thereof.

BACKGROUND ART

Recently, a large number of measurements using immune response are carried out in the clinical test and the like. However, since conventional methods require a complicated operation or a labeling substance, there is used an immunosensor which utilizes a surface plasmon resonance (SPR) capable of detecting change of a ligand with high sensitivity without requiring a labeling substance.

In a measurement chip commonly used for a measurement device employing such surface plasmon resonance (a surface plasmon resonance biosensor), porous materials are formed on a metal membrane coated on a glass substrate, and a physiologically active substance such as an enzyme or an antibody is deposited or immobilized on the surface of these porous materials and/or within these porous materials. Examples of these porous materials include a textile fabric, a knitted fabric and a nonwoven fabric which are composed of synthetic fibers, natural fibers, inorganic fibers etc., and also porous inorganic or organic materials (see Japanese Patent Application Laying-Open (kokai) No. 3-164195). Moreover, in a commercial product (for BIAcore 2000, Pharmacia Biosensor), carboxy methyl dextran is used as a porous material.

As a method for immobilizing a physiologically active substance on a metal membrane, LB (Langmuir-Blodgett) method may be used (see Japanese Patent Application Laying-Open (kokai) No. 5-288672), but this method has a problem in that the binding between an LB membrane and a metal membrane is so weak that the LB membrane falls off together with the physiologically active substance.

Further, Japanese Patent Application Laying-Open (kokai) No. 10-267834 discloses a method for producing an SPR sensor chip by forming an organic silicon membrane on a gold surface using a silane coupling agent, and chemically modifying the gold surface with, for example, a protein using a functional group of a silane coupling agent such as an amino group, carboxyl group, mercapto group and further using a bifunctional reagent. However, in this method, reactivity of the gold surface with the silane coupling agent is so low that an organic silicon membrane cannot be produced with good reproducibility. Moreover, Japanese Patent No. 2815120 discloses a method for introducing a functional group such as a carboxyl group or an amino group onto the surface of gold using a mercapto group.

DISCLOSURE OF THE INVENTION

An object to be achieved by the present invention is to solve the above-stated problems of the prior art. That is, an object of the present invention is to provide a measurement chip for a surface plasmon resonance biosensor which can provide good sensitivity and can be easily produced.

As a result of thorough studies directed to achieve the above object, the present inventors have found that good sensitivity can be obtained by forming an organic silicon membrane which is immobilized onto a metal membrane via a mercapto group, and then immobilizing a physiologically active substance to the organic silicon membrane via a functional group, and thereby completing the present invention.

Thus, according to the present invention, there is provided a measurement chip for a surface plasmon resonance biosensor, which comprises a transparent substrate, a metal membrane located on the transparent substrate and an organic silicon membrane immobilized on the metal membrane and in which the organic silicon membrane is immobilized on the metal membrane via a functional group capable of binding with atoms on the surface of a metal.

Preferably, the organic silicon membrane is a membrane formed by at least one or more types of silane coupling agents which contain a functional group capable of binding with atoms on the surface of a metal.

Preferably, the organic silicon membrane is a membrane formed by a mixture of at least one or more types of silane coupling agents which contain a functional group capable of binding with atoms on the surface of a metal, and at least one or more types of silane coupling agents which contain a functional group capable of binding with physiologically active substances.

Preferably, the functional group capable of binding with atoms on the surface of a metal is a disulfide group, a sulfide group, a diselenide group, a selenide group, a mercapto group, a nitrile group, an isonitrile group, a nitro group, a selenol group, a group derived from a trivalent phosphate compound, an isothiocyanate group, a xanthate group, a thiocarbamate group, a phosphine group, a thio acid group or a dithioic acid group, and particularly preferably a mercapto group.

Preferably, the organic silicon membrane is a membrane formed by a mixture of at least one or more types of silane coupling agents that contain a mercapto group, and at least one or more types of silane coupling agents that contain an amino group.

According to another aspect of the present invention, there is provided a measurement chip for a surface plasmon resonance biosensor wherein a bifunctional reagent is further bound to the organic silicon membrane.

The preferred bifunctional reagent is a disulfone compound represented by the following formula:

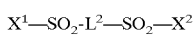

wherein $X^1$ and $X^2$ independently represent —$CR^1$=$CR^2R^3$ or —$CHR^1$—$CR^2R^3Y$; $R^1$, $R^2$ and $R^3$ independently represent an atom or a group selected from a group consisting of a hydrogen atom, an alkyl group having a carbon number of 1 to 6, an aryl group having a carbon number of 6 to 20, and an aralkyl group which contains an alkyl chain having a carbon number of 1 to 6 and has a total carbon number of 7 to 26; Y represents an atom or a group selected from a group consisting of a halogen atom, —$OSO_2R^{11}$, —$OCOR^{12}$, —$OSO_3M$ and a quaternary pyridinium group; $R^{11}$ represents a group selected from a group consisting of an alkyl group having a carbon number of 1 to 6, an aryl group having a carbon number of 6 to 20, and an aralkyl group which contains an alkyl chain having a carbon number of 1 to 6 and has a total carbon number of 7 to 26; $R^{12}$ represents a group selected from a group consisting of an alkyl group having a carbon number of 1 to 6 and an halogenated alkyl group having a carbon number of 1 to 6; M represents an atom or a group selected from a group consisting of a hydrogen atom, an alkali metal atom and an ammonium group; and $L^2$ represents a linking group.

According to further another aspect of the present invention, there is provided a measurement chip for a surface plasmon resonance biosensor as mentioned above, wherein a physiologically active substance is immobilized to an organic silicon membrane directly or via a bifunctional reagent.

According to further another aspect of the present invention, there is provided a method for producing a measurement chip for a surface plasmon resonance biosensor, which comprises the step of treating a metal membrane located on a transparent substrate with a mixture of at least one or more types of silane coupling agents which contain a functional group capable of binding with atoms on the metal surface and at least one or more types of silane coupling agents which contain a functional group capable of binding with physiologically active substances, and thereby forming an organic silicon membrane on the metal membrane.

According to further another aspect of the present invention, there is provided a method for detecting and/or measuring a substance which interacts with a physiologically active substance, which comprises the steps of contacting a surface plasmon resonance biosensor having a physiologically active substance immobilized thereon according to the present invention with a sample containing a target substance; and detecting and/or measuring interaction between the physiologically active substance immobilized on the biosensor and the target substance.

DETAILED DESCRIPTION OF THE INVENTION

The embodiments of the present invention and methods for carrying out the present invention will be described in detail below.

The measurement chip for a biosensor of the present invention is characterized in that it comprises a transparent substrate, a metal membrane located on the transparent substrate, and an organic silicon membrane immobilized on the metal membrane, and the organic silicon membrane is immobilized on the metal membrane via a functional group capable of binding with atoms on the metal surface.

The measurement chip for a biosensor of the present invention can be used, for example, as a measurement chip for a surface plasmon resonance biosensor.

The measurement chip for a surface plasmon resonance biosensor is a chip which is used in a surface plasmon resonance biosensor, and refers to a member comprising a portion for transmitting and reflecting light emitted from the sensor and another portion for immobilizing a physiologically active substance. The member may be fixed to the body of the above sensor, or may be removable.

The phenomenon of surface plasmon resonance is based on that the intensity of monochromatic light reflected from a boundary between an optically transparent substance such as glass and a thin layer of metal is dependent on the refractive index of a sample located at the irradiation side of the metal. Therefore, a sample can be analyzed by measuring the intensity of monochromatic light reflected.

The measurement chip for a biosensor of the present invention is produced by treating a metal membrane with a silane coupling agent defined in the present specification.

In the present invention, a metal membrane is located on a transparent substrate. The term "located on a substrate" refers to the case where a metal membrane is located in such a way that it is in direct contact with the substrate, as well as the case where a metal membrane is located on the substrate via another layer without being in direct contact with the substrate.

Any substrate for a surface plasmon resonance biosensor can be used in the present invention, so far as it is applicable to an immobilization method. Generally, substrates that can be used herein are those made of materials transparent to a laser beam, such as glass, polyethylene terephthalate and polycarbonate. Such a substrate is preferably made of a material which is not anisotropic to polarized light, and has excellent workability. The thickness of the substrate is not particularly limited, and is normally about 0.1 to 20 mm.

Examples of a metal membrane for the measurement chip for a biosensor of the present invention are not specifically limited when it is used for a surface plasmon resonance biosensor, so far as they can bring about surface plasmon resonance. Examples of a metal type that can be applied for the metal membrane include gold, silver, copper, aluminum, and platinum. These metals can be used alone or in combination. Furthermore, taking the adherence of the metal to the above substrate into account, an interstitial layer of chromium or the like may be provided between the substrate and the layer of gold, silver etc.

The thickness of the metal membrane is not particularly limited. For example, when the metal membrane is used for a surface plasmon resonance biosensor, the thickness is preferably 100 to 2,000 angstrom, and particularly preferably, 200 to 600 angstrom. When the thickness is more than 3,000 angstrom, it becomes impossible to sufficiently detect the surface plasmon phenomenon of the medium. When an interstitial layer of chromium or the like is provided, the thickness of the interstitial layer is preferably 5 to 50 angstrom.

The formation of a metal membrane may be performed according to standard techniques such as sputtering, evaporation, ion plating, electroplating and electroless plating.

In the measurement chip for a biosensor of the present invention, an organic silicon membrane is immobilized on a metal membrane. Specifically, the organic silicon membrane is immobilized on the metal membrane via a functional group capable of binding with atoms on the metal surface.

The term "immobilized on the metal membrane via a functional group capable of binding with atoms on the metal surface" in the present invention refers to the state where a functional groups such as a mercapto group capable of binding with atoms on the metal surface are present on the first layer of the metal surface; and a membrane composed of a polymer which contain Si—O bond and Si—C bond within the molecule are present on the second layer thereon. Such an organic silicon membrane can be formed with, for example, at least one or more types of silane coupling agents which contain a functional group capable of binding with atoms on the metal surface. The silane coupling agent refers to an organic silicon compound which contains in its molecule an organic functional group having affinity to an organic material, such as a vinyl group, epoxy group, amino group and mercapto group, and contains a hydrolytic group having affinity to an inorganic material, such as a methoxy group and ethoxy group.

The organic silicon membrane in the present invention is preferably a membrane which is formed by a mixture of at least one or more types of silane coupling agents which contain a functional groups (for example, a mercapto group) capable of binding with atoms on the metal surface, and at least one or more types of silane coupling agents which contain a functional group (for example, an amino group) capable of binding with physiologically active substances.

The mixing ratio (molar ratio) of at least one or more types of silane coupling agents which contain a functional group capable of binding with atoms on the metal surface and at least one or more types of silane coupling agents which contain a functional group capable of binding with physiologically active substances is not particularly limited, and preferably ranges from 1:10 to 10:1, more preferably 1:5 to 5:1, and further more preferably 1:2 to 2:1.

The first silane coupling agent used in the present invention is an organic silicon compound which contains, within its molecules, a functional group capable of binding with atoms on a metal surface. Examples of the functional group capable of binding with atoms on a metal surface include disulfide group (—SS—), sulfide (—S—), diselenide (—SeSe—), selenide (—Se—), thiol (—SH), nitrile (—CN), isonitrile, nitro (—NO$_2$), selenol (—SeH), trivalent phosphate compound, isothiocyanate, xanthate, thiocarbamate, phosphine, thio acid, and dithioic acid (—COSH, —CSSH), and particularly preferably a mercapto group. Specifically, 3-mercaptopropyltrimethoxysilane, dimethoxy-3-mercaptopropylmethylsilane and the like may be used alone or in combination as the first silane coupling agent.

The second silane coupling agent used in the present invention refers to an organic silicon compound which contains, within its molecules, a functional group (for example, an amino group) capable of binding with a physiologically active substance. Specifically, 3-aminopropyltriethoxysilane, 3-aminopropyltrimethoxysilane, 3-aminopropyldiethoxymethylsilane, 3-(2-aminoethylaminopropyl)trimethoxysilane, 3-(2-aminoethylaminopropyl)dimethoxymethylsilane and the like may be used alone or in combination.

Moreover, in order to immobilize a physiologically active substance via a chemical bond, a functional group capable of binding with a physiologically active substance may be additionally introduced. For example, an amino group can be introduced onto the surface of gold by treating the surface of gold with 3-mercaptopropyltrimethoxysilane, followed by treating again with an amine silane coupling agent such as 3-aminopropryltriethoxysilane. Examples of an amine silane coupling agent include 3-aminopropyltrimethoxysilane, 3-aminopropyldiethoxymethylsilane, 3-(2-aminoethylaminopropyl)trimethoxysilane and 3-(2-aminoethylaminopropyl)dimethoxymethylsilane.

Alternatively, for example, an amino group can be introduced onto a surface in single step by treating the surface of gold with a mixture of 3-mercaptopropyltrimethoxysilane and 3-aminopropyltriethoxysilane simultaneously.

The organic silicon membrane is preferably a monomolecular layer membrane wherein silicon atoms do not overlap in up and down direction. By using the monomolecular layer membrane, the distance between a surface where incoming light reflects off and a target substance which interacts with a physiologically active substance can be reduced. Thereby, good sensitivity can be obtained, and the amount of a silane coupling agent used can be reduced to minimum, and costs can be reduced.

Further, the organic silicon membrane preferably has a finely-packed structure. The finely-packed structure refers to that the network structure of Si and O which constitute an organic silicon membrane is fine enough to avoid penetration of other molecules into the structure. The use of the finely-packed structure enables uniform immobilization of physiologically active substances at a high density, and can improve the sensitivity for measurement. Whether or not an organic silicon membrane has a finely-packed structure can be confirmed by the following method. The organic silicon membrane is formed on a metal membrane using an appropriate propylethoxysilane agent. When the surface uniformly repels droplets of distilled water dropped from a syringe, the organic silicon membrane has a finely-packed structure. When the surface repels the water only partially, the organic silicon membrane does not have a finely-packed structure, and air gaps are predicted to be present in the network structure of Si and O.

The organic silicon membranes can be formed by using the above-mentioned silane coupling agent. Specifically, the membrane can be formed by a method which exposes a metal membrane in the saturated steam of a silane coupling agent for a certain time (saturated steam method), a method which immerses a metal membrane in a solution containing a silane coupling agent for a certain time (immersion method), a method which uses a spin coater (spin-coating method), a method which uses a gravure printer (gravure method) and the like. Any of these methods may be used in the present invention. In particular, the saturated steam method is preferably used to form a monomolecular layer membrane having a finely-packed structure In the saturated steam method, temperature and humidity upon exposure affect the formation of a monomolecular layer structure and a finely-packed structure, but exposure time is the most important factor. When the exposure time is too long, a monomolecular layer structure cannot be obtained. When the exposure time is too short, a finely-packed structure cannot be obtained. Normally, the exposure time is preferably 1 to 600 minutes, and more preferably 15 to 90 minutes.

The silane coupling agent used in the present invention has the following advantages:
(1) Since a physiologically active substance can be immobilized at a position extremely close to a metal membrane, measurement sensitivity can be greatly improved as compared with the conventional immobilization methods.
(2) Surface treatment is simple, and a large amount of surface treatment can be carried out at one time.
(3) By selecting the substituent Y which is a functional group capable of covalently binding with a physiologically active substance, it becomes possible to perform chemical modifications such as surface reforming or introduction of another functional group.

The measurement chip for a biosensor is used in such a manner that a physiologically active substance is immobilized directly or via a bifunctional reagent to a metal surface treated with the silane coupling agent. As a means for immobilizing a target physiologically active substance, covalent binding via a bifunctional reagent is preferred.

Examples of the representative bifunctional reagent include glutaraldehyde, periodic acid, N,N'-o-phenylenedimaleimide, N-succinimydyl-4-(N-maleimidemethyl) cyclohexane-1-carboxylate, N-succinimydylmaleimide acetic acid, N-succinimydyl-4-maleimide butyric acid, N-succinimydyl-6-maleimide hexanoic acid, N-sulfosuccinimydyl-4-maleimidemethylcyclohexane-1-carboxylic acid, N-sulfosuccinimydyl-3-maleimide benzoic acid, sodium N-(4-maleimidebutyloxy)sulfosuccinimide salt, sodium N-(6-maleimidecaproyloxy) sulfosuccinimide salt, sodium N-(8-maleimidecapryloxy)sulfosuccinimide salt, sodium N-(11-maleimideundecanoyloxy)sulfosuccinimide salt, N-[2-(1-piperazinyl) ethyl]malemide dihydrochloride, and disulfone compound (for example, divinyl sulfone compound). They may be used alone or in combination.

The disulfone compound used as a bifunctional reagent in the present invention is preferably a disulfone compound represented by the following formula (1):

(1)

wherein $X^1$ and $X^2$ independently represent $-CR^1=CR^2R^3$ or $-CHR^1-CR^2R^3Y$ (a reactive precursor group); $R^1$, $R^2$ and $R^3$ independently represent an atom or a group selected from a group consisting of a hydrogen atom, an alkyl group having a carbon number of 1 to 6, an aryl group having a carbon number of 6 to 20, and an aralkyl group which contains an alkyl chain having a carbon number of 1 to 6 and has a total carbon number of 7 to 26; Y represents an atom or a group selected from a group consisting of a halogen atom, $-OSO_2R^{11}$, $-OCOR^{12}$, $-OSO_3M$ and a quaternary pyridinium group; $R^{11}$ represents a group selected from a group consisting of an alkyl group having a carbon number of 1 to 6, an aryl group having a carbon number of 6 to 20, and an aralkyl group which contains an alkyl chain having a carbon number of 1 to 6 and has a total carbon number of 7 to 26; $R^{12}$ represents a group selected from a group consisting of an alkyl group having a carbon number of 1 to 6 and an halogenated alkyl group having a carbon number of 1 to 6; M represents an atom or a group selected from a group consisting of a hydrogen atom, an alkali metal atom and an ammonium group; and $L^2$ represents a linking group.

The disulfone compound represented by the above formula (1) can be introduced onto a metal membrane by contacting the compound with the metal membrane having an organic silicon membrane immobilized thereon under, for example, an aqueous atmosphere.

Typical examples of the disulfone compound preferably used in the present invention are shown below. A mixture of two or more types of disulfone compounds may be used.

(S1)

(S2)

(S3)

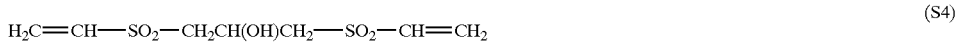
(S4)

(S5)

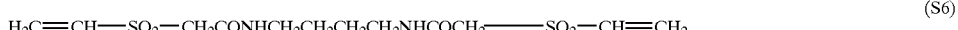
(S6)

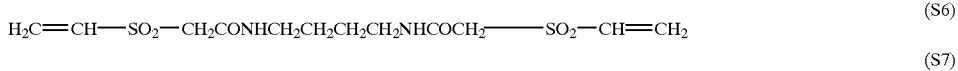
(S7)

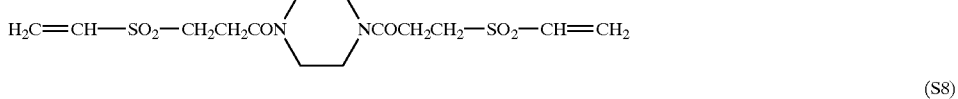
(S8)

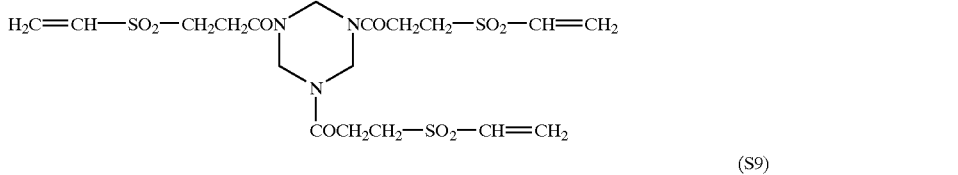
(S9)

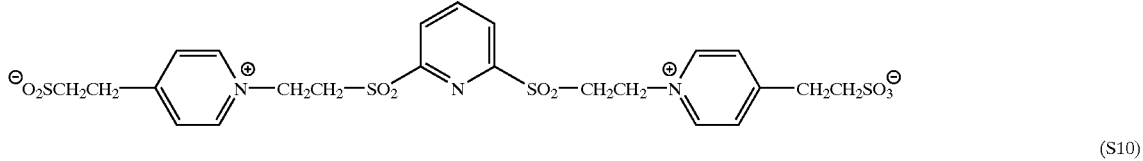
(S10)

(S11)

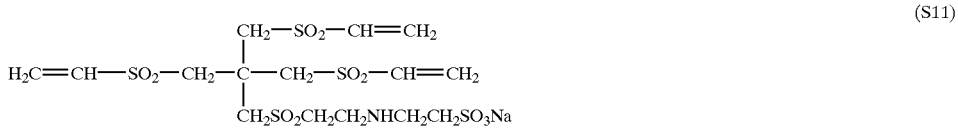
(S12)

(S13)

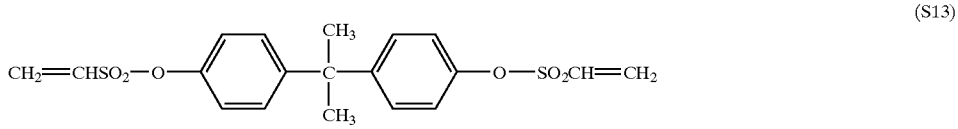

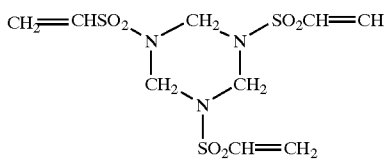

(S14)

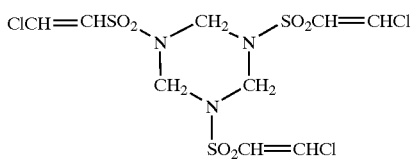

(S15)

A typical example of the disulfone compound represented by the above formula (1) is 1,2-bis (vinylsulfonylacetamide) ethane [corresponding to the above S1].

Methods for synthesizing the disulfone compound used in the present invention are described in detail in various official gazettes including Japanese Patent Publication (Kokoku) Nos. 47-2429 and 50-35807, and Japanese Patent Application Laying-Open (Kokai) Nos. 49-24435, 53-41551 and 59-18944.

The physiologically active substance to be immobilized to the measurement chip for a biosensor of the present invention is not particularly limited, as long as it interacts with the target substance. Examples of the physiologically active substances include immune protein, enzyme, microorganism, nucleic acid, low molecular organic compound, non-immune protein, immunoglobulin binding-protein, sugar-binding protein, sugar chain which recognizes sugar, fatty acid or fatty acid ester, and polypeptide or oligopeptide capable of binding to a ligand.

Examples of an immune protein include an antibody and a hapten, the antigen of which is a target substance. Examples of an antibody to be used include various immunoglobulins such as IgG; IgM, IgA, IgE and IgD. Specifically, when a target substance is human serum albumin, an anti-human serum albumin antibody can be used as an antibody. When a pesticide, an insecticide, methicillin resistant *Staphylococcus aureus*, an antibiotic, narcotic, cocaine, heroin, crack or the like is used as an antigen, there can be applied, for example, an anti-atrazine antibody, an anti-kanamycin antibody, an anti-metamphetamine antibody or antibodies against O antigens 26, 86, 55, ill, 157 etc. in enteropathogenic *Escherichia coli*.

The enzyme to be used herein is not particularly limited, as long as it shows activity against a target substance or a substance metabolized from the target substance. Various enzymes such as oxidoreductase, hydrolase, isomerase, lyase, or synthetase can be used. Specifically, when the target substance is glucose, glucose oxidase can be used. When the target substance is cholesterol, cholesterol oxidase can be used. Further, when a pesticide, an insecticide, methicillin resistant *Staphylococcus aureus*, an antibiotic, narcotic, cocaine, heroin or crack or the like is used as a target substance, enzymes such as acetylcholin esterase, catecholamine esterase, noradrenaline esterase and dopamine esterase, which specifically react with a substance metabolized from such a target substance, can be used.

The microorganisms are not particularly limited, and various microorganisms such as *Escherichia coli* can be used.

Any nucleic acid which complementarily hybridizes to a nucleic acid acting as a target substance can be used. As a nucleic acid, both DNA (including cDNA) and RNA can be used. Types of DNA are not particularly limited, and any of naturally occurring DNA, recombinant DNA prepared by gene recombination techniques and chemically synthesized DNA can be used.

As a low molecular organic compound, any compound that can be synthesized by a common organic chemical synthetic method can be used. It is preferred to use a compound having a functional group capable of binding to the linker compound of formula I used in the present invention directly or via a crosslinking compound.

The non-immune protein to be used herein is not particularly limited, and avidin (streptavidin), biotin, a receptor etc. can be used.

Examples of the immunoglobulin binding-protein to be used herein include protein A, protein G, and a rheumatoid factor (RF).

Examples of a sugar-binding protein include lectin.

Examples of fatty acid or fatty acid ester include stearic acid, arachidic acid, behenic acid, ethyl stearate, ethyl arachidate, and ethyl behenate.

The present invention is further explained by the following examples. The present invention is not limited by these examples.

EXAMPLES

Example 1

Preparation of Sensor Chip

The thin membrane chip of gold of SIA Kit Au (BIAcore) was immersed for 24 hours in 1% aqueous solution of a 1:1 mixture of 3-mercaptopropyltrimethoxysilane and 3-aminopropyltriethoxysilane (Shin-Etsu Chemical Co., Ltd.). Then, the surface was washed with distilled water, and then heated at 110° C. for 15 minutes. The product was immersed for 1 hour in a phosphate buffer solution (pH 8.5) of 5% by weight of 1,2-bis(vinylsulfonylacetamide)ethane, and was then removed from the solution, washed with acetonitrile, and then dried under reduced pressure for 1 hour, thereby obtaining a sensor chip having a surface on which vinylsulfonyl groups were introduced.

Example 2

Measurement

The sensor chip prepared in (1) above was placed on the cartridge block of a commercially available surface plasmon resonance biosensor (Pharmacia Biosensor, BIAcore 2000). Anti-human IgG antibody (1 mg/ml) was poured into the sensor at a flow rate of 1 u 1/minute for 1 hour to immobilize the anti-human IgG on the surface of mercapto/organic silicon membrane. Subsequently, blocking with 10 mM ethanolamine was performed, and then 0.1N hydrochloric acid (5 µl) was poured into the measurement cell at a flow rate of 5 µl/minute in order to wash away unreacted antibodies.

Light intensity was measured to obtain resonance signals (RU) while human IgG diluted to 0.01, 0.1, 1 and 10 µg/ml was poured at a flow rate of 5 µl/minutes for 10 minutes into the measurement cell containing the measurement chips with antibodies immobilized thereto. As a comparative example, a similar experiment was performed using a commercially available Sensor Chip C1 (BIAcore). The results are shown in Table 1 below. The numeric unit in Table 1 represents resonance signal (RU). As is understood from the results in Table 1, by using the sensor chip of the present invention, a target substance can be measured with better sensitivity than by using the sensor chip of the comparative example. In particular, even if only a small amount of a physiologically active substance is immobilized, a target substance can be measured with good sensitivity.

TABLE 1

| IgG concentration (µg/ml) | Chip of the Invention | Chip of Comparative Example |
|---|---|---|
| 0 | 1 | 1 |
| 0.01 | 113 | 12 |
| 0.1 | 1216 | 115 |
| 1 | 4200 | 809 |
| 10 | 5000 | 1100 |

Effect of the Invention

The measurement chip for a biosensor of the present invention can easily be produced. Using the measurement chip of the present invention, a target substance can be measured with good sensitivity, even if only a small amount of physiologically active substance is immobilized.

What is claimed are:

1. A measurement chip for a surface plasmon resonance biosensor, which comprises a transparent substrate, a metal membrane located on the transparent substrate and an organic silicon membrane immobilized on the metal membrane via a functional group capable of binding with atoms on the surface of a metal, and wherein a bifunctional reagent, which contain a functional group capable of binding with physiologically active compound, is further bound to the organic silicon membrane, said bifunctional reagent is a disulfone compound, represented by the following formula:

$X^1\!-\!SO_2\!-\!L^2\!-\!SO_2\!-\!X^2$,

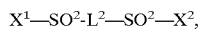

wherein $X^1$ and $X^2$ independently represent $-CR^1\!=\!CR^2R^3$ or $-CHR^1\!-\!CR^2R^3Y$; $CR^1\!=\!CR^2R^3$ independently represent an atom or a group selected from the group consisting of a hydrogen atom, an alkyl group having a carbon number of 1 to 6, an aryl group having a carbon number of 6 to 20, and an aralkyl group which contains an alkyl chain having a carbon number of 1 to 6 and has a total carbon number of 7 to 26; Y represents an atom or a group selected from the group consisting of a halogen atom, $-OSO_2R^{11}$, $-OSO_2R^{12}$, $-OSO_3M$ and a quaternary group consisting of a halogen atom, $-OSO_2R^{11}$, $-OSO_2R^{12}$, $-OSO_3M$ and a quaternary pyridinium group; $R^{11}$ represents a group selected from the group consisting of an alkyl group having a carbon number of 1 to 6, an aryl group having a carbon number of 6 to 20, and an aralkyl group which contains an alkyl chain having a carbon number of 1 to 6 and has a total carbon number of 7 to 26; $R^{12}$ represents a group selected from the group consisting of an alkyl group having a carbon number of 1 to 6 and a halogenated alkyl group having a carbon number of 1 to 6; M represents an atom or a group selected from the group consisting of a hydrogen atom, an alkali metal atom and an ammonium group; and $L^2$ represents a linking group.

2. The measurement chip for a surface plasmon resonance biosensor according to claim 1, wherein the organic silicon membrane is a membrane formed by at least one or more types of silane coupling agents which contain a functional group capable of binding with atoms on the surface of a metal.

3. The measurement chip for a surface plasmon resonance biosensor according to claim 1, wherein the functional group capable of binding with atoms on the surface of a metal is a disulfide group, a sulfide group, a diselenide group, a selenide group, a mercapto group, a nitrile group, an isonitrile group, a nitro group, a selenol group, a group derived from a trivalent phosphate compound, an isothiocyanate group, a xanthate group, a thiocarbamate group, a phosphine group, a thio acid group or a dithioic acid group.

4. The measurement chip for a surface plasmon resonance biosensor according to claim 3, wherein the functional group capable of binding with atoms on the surface of a metal is a mercapto group.

5. The measurement chip for a surface plasmon resonance biosensor according to claim 1, wherein the organic silicon membrane is a membrane formed by a mixture of at least one or more types of silane coupling agents that contain a mercapto group, and at least one or more types of silane coupling agents that contain an amino group.

6. The measurement chip for a surface plasmon resonance biosensor according to claim 1, wherein a physiologically active substance is immobilized to the organic silicon membrane via the bifunctional reagent.

7. A method for producing a measurement chip for a surface plasmon resonance biosensor according to claim 1, which comprises the step of treating a metal membrane located on a transparent substrate with a mixture of at least one or more types of silane coupling agents which contain a functional group capable of binding with atoms on the metal surface; thereby forming an organic silicon membrane immobilized on the metal membrane, and further contacting the metal membrane with the immobilized organic silicon membrane with a disulfone compound, represented by the following formula:

$X^1\!-\!SO_2\!-\!L^2\!-\!SO_2\!-\!X^2$,

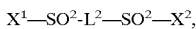

wherein $X^1$ and $X^2$ independently represent $-CR^1\!=\!CR^2R^3$ or $-CHR^1\!-\!CR^2R^3Y$; $CR^1\!=\!CR^2R^3$ independently represent an atom or a group selected from the group consisting of a hydrogen atom, an alkyl group having a carbon number of 1 to 6 an aryl group having a carbon number of 6 to 20, and an aralkyl group which contains an alkyl chain having a carbon number of 1 to 6 group consisting of a halogen atom, $-OSO_2R^{11}$, $-OSO_2R^{12}$, $-OSO_3M$ and a quaternary pyridinium group; $R^{11}$ represents a group selected from the group consisting of an alkyl group having a carbon number of 1 to 6, an aryl group having a carbon number of 6 to 20, and an aralkyl group which contains an alkyl chain having a carbon number of 1 to 6 and has a total carbon number of 7 to 26; $R^{12}$ represents a group selected from the group consisting of an alkyl group having a carbon number of 1 to 6 and a halogenated alkyl group having a carbon number of 1 to 6; M represents an atom or a group selected from the group consisting of a hydrogen atom, an alkali metal atom and an ammonium group; and $L^2$ represents a linking group.

8. A method for detecting and/or measuring a substance which interacts with a physiologically active substance, which comprises the steps of contacting a surface plasmon resonance biosensor, comprising the measurement chip of claim 1 and having a physiologically active substance immobilized on the chip, with a sample containing a target substance; and detecting and/or measuring interaction between the physiologically active substance immobilized on the biosensor and the target substance.

* * * * *